(12) United States Patent
Rizzi

(10) Patent No.: US 9,919,281 B2
(45) Date of Patent: Mar. 20, 2018

(54) SHELL AND TUBE HEAT EXCHANGER WITH A SHELL HAVING A POLYGONAL SECTION

(71) Applicant: Casale SA, Lugano (CH)

(72) Inventor: Enrico Rizzi, Casnate con Bernate (IT)

(73) Assignee: Casale SA, Lugano (CH)

( * ) Notice: Subject to any disclaimer, the term of this patent is extended or adjusted under 35 U.S.C. 154(b) by 115 days.

(21) Appl. No.: 15/106,060

(22) PCT Filed: Dec. 16, 2014

(86) PCT No.: PCT/EP2014/077902
§ 371 (c)(1),
(2) Date: Jun. 17, 2016

(87) PCT Pub. No.: WO2015/091442
PCT Pub. Date: Jun. 25, 2015

(65) Prior Publication Data
US 2016/0303533 A1    Oct. 20, 2016

(30) Foreign Application Priority Data
Dec. 18, 2013    (EP) ..................................... 13197955

(51) Int. Cl.
*B01J 19/00* (2006.01)
*B01J 19/24* (2006.01)
(Continued)

(52) U.S. Cl.
CPC ....... *B01J 19/0013* (2013.01); *B01J 19/2415* (2013.01); *C01C 1/02* (2013.01);
(Continued)

(58) Field of Classification Search
CPC .... B01J 19/00; B01J 19/0006; B01J 19/0013; B01J 19/24; B01J 19/2415;
(Continued)

(56) References Cited

U.S. PATENT DOCUMENTS 3,797,569 A    3/1974    Meder et al.
4,147,208 A    4/1979    Naegelin
(Continued)

FOREIGN PATENT DOCUMENTS

CN    201772781 U    3/2011
DE    1 501 045 A1    4/1969
(Continued)

OTHER PUBLICATIONS

International Search Report issued in connection with PCT/EP2014/077902.
(Continued)

*Primary Examiner* — Natasha Young
(74) *Attorney, Agent, or Firm* — Akerman LLP

(57) ABSTRACT

Heat exchanger comprising a tube bundle (1) and a shell (2) which surrounds said tube bundle, said tube bundle comprising tubes (3) arranged with a square or triangular pitch, wherein said shell (2) has a cross-section, in a plane perpendicular to said tubes, having the form of an irregular polygon; said irregular cross-sectional polygon has a number of sides which is a multiple of three or multiple of four for tube bundles with a triangular or square pitch, respectively; the sides of said cross-sectional polygon are parallel to the directional lines of the tubes.

9 Claims, 5 Drawing Sheets

(51) Int. Cl.
  *F28D 7/00* (2006.01)
  *F28D 7/16* (2006.01)
  *F28D 21/00* (2006.01)
  *F28F 9/00* (2006.01)
  *C01C 1/02* (2006.01)
  *C07C 29/00* (2006.01)
  *C01C 1/00* (2006.01)

(52) U.S. Cl.
  CPC .............. *C07C 29/00* (2013.01); *F28D 7/163* (2013.01); *F28F 9/00* (2013.01); *B01J 2219/00081* (2013.01); *B01J 2219/192* (2013.01); *F28D 2021/0022* (2013.01)

(58) Field of Classification Search
  CPC .... B01J 2219/00049; B01J 2219/00051; B01J 2219/00074; B01J 2219/00076; B01J 2219/00081; B01J 2219/19; B01J 2219/192; C01C 1/00; C01C 1/02; C07C 29/00; F28D 7/00; F28D 7/16; F28D 7/163; F28D 2021/0019; F28D 2021/0022; F28D 21/00; F28F 9/00
  See application file for complete search history.

(56) References Cited

U.S. PATENT DOCUMENTS

| | | | | |
|---|---|---|---|---|
| 4,265,301 | A | * | 5/1981 | Anderson ................ F28D 7/16 165/162 |
| 5,251,693 | A | | 10/1993 | Zifferer |
| 7,758,824 | B2 | * | 7/2010 | Hugues ..................... B01J 8/22 165/145 |
| 2009/0218081 | A1 | | 9/2009 | Mathew et al. |

FOREIGN PATENT DOCUMENTS

| | | |
|---|---|---|
| DE | 100 49 970 A1 | 4/2002 |
| EP | 0 851 197 A2 | 7/1998 |
| EP | 2 600 092 A1 | 6/2013 |
| JP | S59-229186 A | 12/1984 |
| JP | S60-223992 A | 11/1985 |

OTHER PUBLICATIONS

International Preliminary Report on Patentability issued in connection with PCT/EP2014/077902.

* cited by examiner

SHELL AND TUBE HEAT EXCHANGER WITH A SHELL HAVING A POLYGONAL SECTION

This application is a national phase of PCT/EP2014/077902, now WO 2015/091442, filed Dec. 16, 2014, and claims priority to EP 13197955.1, filed Dec. 18, 2013, the entire contents of both of which are hereby incorporated by reference.

FIELD OF APPLICATION

The invention relates to tube heat exchangers comprising a tube bundle inside a shell (shell and tube).

PRIOR ART

Exchangers comprising a tube bundle are always contained inside a shell for high pressure (high pressure shell), which is able to withstand the pressure of the process fluid, or in any case they are contained inside reactors, which are also equipped with a high-pressure shell.

For reasons of mechanical strength, these shells have a circular cross-section. The internals of the aforementioned reactors also generally have axial symmetry and consist of concentric cylinders with a circular cross-section. The shell and tube exchangers contained inside the aforementioned apparatus may be provided with their own shell which is generally not subject to a significant pressure difference between inside and outside and which, for this reason, is called a low-pressure shell. In the prior art, said low-pressure shell is also generally cylindrical with a circular cross-section; the tubes are generally arranged with a square or triangular pitch.

The arrangement of the tubes with a square or triangular pitch generates envelope sections of the tubes which do not fully match the circular cross-section. As a result, owing to the cylindrical shape of the shell, there inevitably exist bypass areas between the periphery of the tube bundle and the shell itself.

In fact, tubes arranged with a square or triangular pitch cannot closely match the circular cross-section of the cylindrical shell and the designer must necessarily leave free areas (without tubes) in the vicinity of the shell. Said areas are called "bypass areas" because the fluid which passes through them flows around the bundle instead of flowing through the bundle and as a matter of fact it does not exchange heat with the tubes. These areas are not negligible and in some cases represent as much as 10% or 20% of the overall available cross-section.

The problem is even greater when the diameter of the tubes is relatively large compared to the diameter of the shell. Tubes with a relatively large diameter in fact tend to leave larger bypass areas. The problem is also greater in the case of so-called annular bundles wherein the tubes are arranged substantially in a circular ring around a central duct (for example for downwards or upwards conveying of a flow) because they form bypass areas both on the inner periphery, i.e. close to the central duct, and on the outer periphery close to the shell.

The aforementioned bypass areas for example reduce the performance of the catalytic reactors containing a tube bundle exchanger, for example isothermal reactors or multibed reactors which are intercooled.

In the prior art attempts have been made in certain cases to reduce these drawbacks using shells with a cross-section in the form of a regular polygon, for example hexagonal with tubes in a triangular pitch. These shells, although closely following the arrangement of the tubes and eliminating the bypass areas, do not match the circular cross-section of the high-pressure shells or of the elements forming the internals of the reactor.

As a result the high-pressure shells must be made with a larger diameter than would normally be required. In the hexagonal case for example, the minimum diameter of the applicable shell is given by the circle which circumscribes the hexagon, namely the circle which touches the vertices of said regular polygon.

This results in a non-optimum use of the internal volume of the apparatus.

For example, a shell with a diameter of 1000 mm has an internal cross-section of about 785,000 $mm^2$, while the hexagon inscribed inside has a cross-section of about 650,000 $mm^2$ and the inscribed octagon has a cross-section of about 707,000 $mm^2$. In the case of a hexagonal shell, compared to a shell with a cross-section of 785,000 $mm^2$, the exchange cross-section available is only 650,000 $mm^2$ (about 83%), which means that about 17% of the cross-section of the apparatus cannot be exploited. Similarly, one may compute that about 10% of the cross-section is not available with an octagonal shell.

The aforementioned values refer to the case where the vertices of the low-pressure shell coincide with the high-pressure shell, a situation which in fact cannot occur for both constructional reasons and process-related reasons; as a result, in practice the increase in diameter of the high-pressure shell is greater than that estimated above.

A description of this prior art may be found in U.S. Pat. No. 5,251,693A, CN 201772781U and JP S59229186A.

In this connection it is important to note that a high-pressure shell is generally expensive and that, for the same design conditions (pressure and temperature), an increase in the diameter of the shell results in an increase in the thickness, with an evident greater weight and hence higher cost. This difference is all the greater the more stringent the design conditions (pressure and temperature) of the apparatus. The cost of the flanges and the cover should also be considered.

For example, considering a cylindrical apparatus made of steel which is 10 m long and designed for a pressure of 5 bar (and 200° C.), a diameter of 500 mm corresponds to a weight of about 430 kg, while a diameter of 1000 mm corresponds to a weight of more than 1100 kg. If it is required to withstand higher pressures, a larger diameter also requires an increase in the thickness with a consequent much greater weight.

SUMMARY OF THE INVENTION

The invention aims to overcome the abovementioned drawbacks. The aims are achieved with a heat exchanger according to the accompanying claim 1.

The idea forming the basis of the invention is to provide the shell with a cross-section of an irregular polygon having sides parallel to the directional lines of the tubes. Said irregular polygon has a number of sides which is a multiple of the number which expresses the arrangement of the tubes, said parameter being equal to 3 for tubes with a triangular pitch and equal to 4 for tubes with a square pitch. This results in a low-pressure shell with a form which may be defined as being staggered or stepped.

The term of "directional lines" of the tubes denotes straight lines in a plane perpendicular to the axis of the tubes (also called the longitudinal axis of the tubes bundle)

passing through the centres of the cross-sections of said tubes. Said directional lines have directions which are spaced at angles of 45° for tubes with a square pitch and spaced at angles of 60° for tubes with a triangular pitch. With reference to a first directional line having a conventional direction of 0°, the directional lines have directions respectively of:

a) 60° and 120° for tubes arranged with a triangular pitch, or b) 45°, 90°, 135° for tubes with a square pitch.

The number of the sides is a multiple of three when the tubes have a triangular pitch and is a multiple of four when the tubes have a square pitch. The sides of said irregular polygon are parallel to planes tangential to the peripheral tubes of the bundle.

If p is the parameter which expresses the arrangement of the tubes, the number of the sides n of the shell may be expressed by the following equation:

$$n = mp$$

where p is equal to 3 for tubes with a triangular pitch and to 4 for tubes with a square pitch;

m is an integer greater than 1.

The cross-section in the form of an irregular polygon, provided according to the invention, results in a good match with a circular cross-section and therefore the walls of the shell remain close to the peripheral tubes and, as a consequence, the bypass areas are small. In catalytic reactors, this advantage is also equivalent to a larger available volume for the catalyst.

A shell according to the invention substantially eliminates the bypass areas and minimizes the diameter of the high-pressure shell in relation to the number of tubes and therefore the heat exchange capacity (duty). The invention thus overcomes the drawbacks of the shell with a circular cross-section and the shell with a regular polygon cross-section, which, although being simple to construct, have the disadvantages of bypass areas and/or a greater diameter compared to the minimum value which is theoretically required.

A shell according to the invention therefore represents an optimum compromise between constructional simplicity and the need to minimize the diameter of the pressurized body. This compromise is all the more advantageous the more critical the design conditions of the high-pressure shell.

A polygon with a large number of sides as is known tends to match closely a circle, i.e. the polygonal shell tends towards the form of a cylindrical shell. The applicant has however found that embodiments with a multiplier m of between 2 and 4 may be satisfactory. In preferred embodiments, the number of sides is equal to 24 for a square pitch and 18 for a triangular pitch.

A number of preferred embodiments of the invention relate to heat exchangers for internals of apparatus having their own shell, for example for internals of chemical reactors. In these applications, the operating pressure is borne by the shell of the apparatus, which may be a conventional cylindrical shell. The shell with a polygonal cross-section (or inner shell) is instead subject to a pressure difference between inside and outside which is relatively small (for example a few bars) and may be referred to as "low-pressure" shell.

Said operating pressure may be, for example, the high pressure necessary for a chemical reaction, such as the synthesis of ammonia or methanol. The difference in pressure to which the inner shell is subject may be due for example to pressure losses.

In some embodiments, the apparatus is provided with a central tube. Embodiments with a central tube are employed for example in chemical reactors for conveying upwards a pre-heated flow after it has initially passed along the shell side. Preferably the central tube also has a stepped form.

In some preferred embodiments the tube bundle comprises baffles for supporting the tubes and preventing vibrations. Said baffles define a suitable configuration of through-openings for the tubes, for example they define elongated slots for respective rows of horizontal, vertical or diagonal tubes. More preferably, adjacent baffles have a configuration of openings for supporting the tubes in different support planes, so as to prevent vibrations in any direction. These constructional elements are known, for example as rod baffles, and do not require a detailed description.

Preferably, the tube bundle is extractable from the shell. This feature, however, is not essential.

The main advantage of the invention consists in the reduction of the bypass areas around the peripheral tubes, which is a consequence of the stepped form of the shell. The faces of the prismatic shell, viewed in cross-section, are lines parallel to the directional lines of the tubes; consequently the said faces of the shell are practically tangential to the peripheral tubes, whether they have a square or triangular pitch. The advantage of the invention is obtained both for cylindrical shells and for shells with the shape of a regular prism, for example with a cross-section in the form of a regular hexagon. Another advantage of the invention is that, for the same number of tubes, the dimensions of the shell may be limited. In apparatus for the internals of exchangers or catalytic reactors, this advantage may result in a gain in terms of useful volume or volume for a catalyst. Other related advantages consist in the lower weight and lower cost.

The advantages will emerge even more clearly with the aid of the detailed description below relating to a number of preferred embodiments.

DETAILED DESCRIPTION

Figure 1:
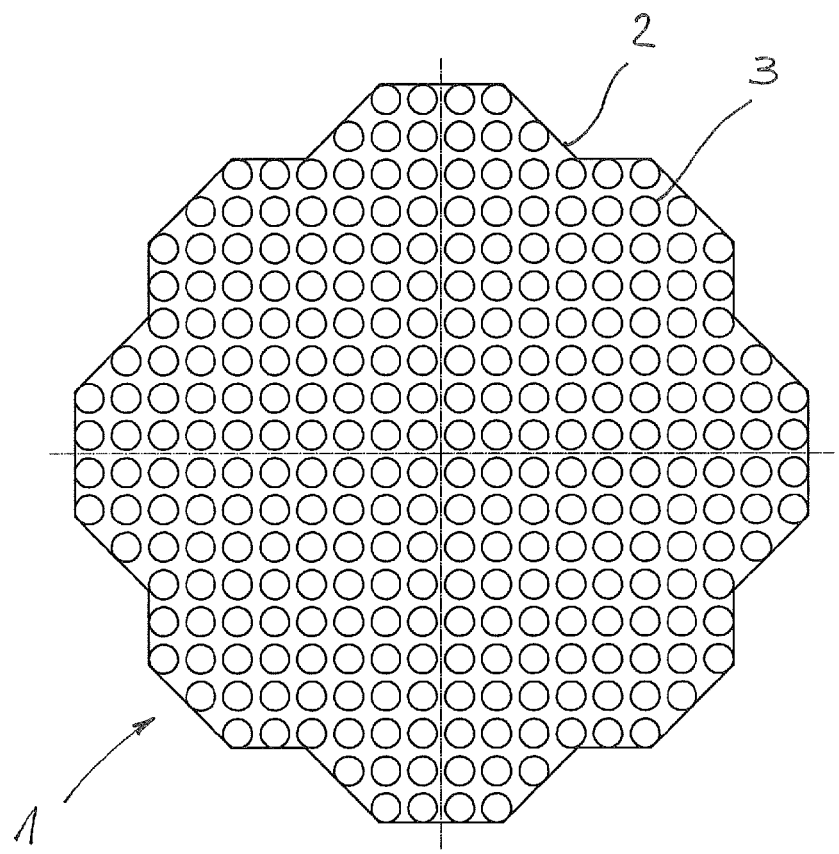
FIG. 1 is a schematic cross-sectional view of a tube apparatus according to a first embodiment of the invention.

FIG. 1 shows schematically a cross-section of a tube bundle 1 with a shell 2. The bundle 1 comprises a plurality of tubes 3 arranged with a square pitch.

Figure 2:
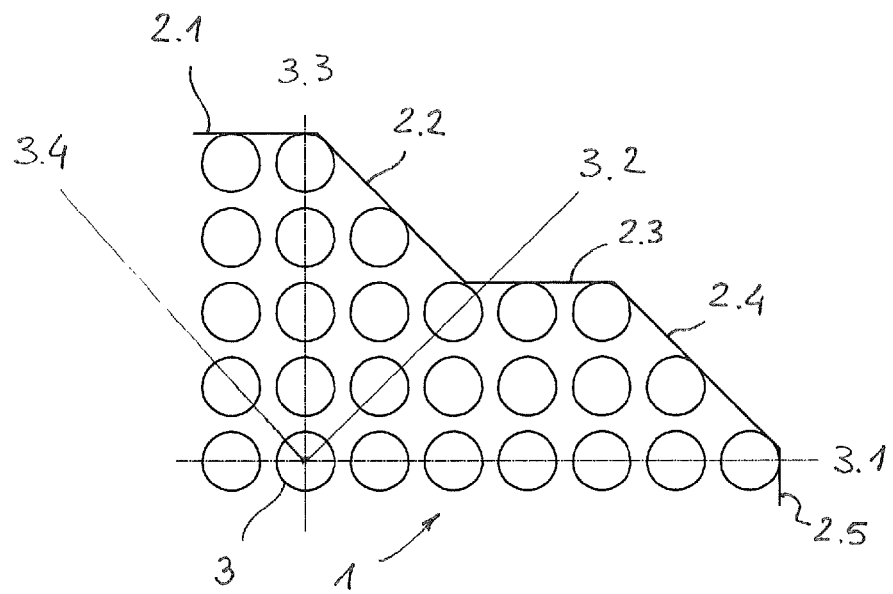
FIG. 2 shows a detail of FIG. 1.

As can be noted from the detail shown in FIG. 2, the axes of four adjacent tubes 3 are arranged in the manner of the vertices of a square. Owing to the square pitch arrangement, the tubes 3 are arranged along directional lines 3.1, 3.2, 3.3 and 3.4 spaced at 45°. For example, taking as a reference a straight line coinciding with the directional line 3.1, the directional lines of the tubes are defined by angles of 0°, 45°, 90° and 135°.

The shell 2 has a cross-section of an irregular polygon. The cross-section is understood as being viewed in a plane perpendicular to the tubes 3, i.e. perpendicular to a longitudinal axis of the tube bundle (corresponding to the plane of FIGS. 1 and 2).

The number n of the sides of said irregular polygon is a multiple of the parameter p which expresses conventionally the arrangement of the tubes 3. Said parameter p is equal to 3 for a triangular pitch and 4 for a square pitch.

In the example shown in FIG. 1 with tubes having a square pitch, the shell 2 is substantially a prism comprising 24 faces. The polygon viewed in cross-section therefore appears as an irregular polygon with 24 sides.

The sides of the cross-sectional polygon of the shell 2 are parallel to directional lines of the tubes. Each side is parallel to one of the directional lines: in FIG. 2 it can be seen for example that the side 2.1 is parallel to the directional line 3.1; the side 2.2 is parallel to the directional line 3.4; the side 2.3 is again parallel to the directional line 3.1; the side 2.4 is parallel to the directional line 3.4; the side 2.5 is parallel to the directional line 3.3.

In other quadrants, as can be noted from FIG. 1, the cross-sectional polygon comprises sides parallel also to the other directional line 3.2.

Looking at FIG. 1 it can be seen that the stepped shell 2 is able to surround a bundle of tubes with a square pitch, such as the bundle 1 shown, without leaving any major bypass areas around the peripheral tubes, unlike a conventional cylindrical shell.

Figure 3:
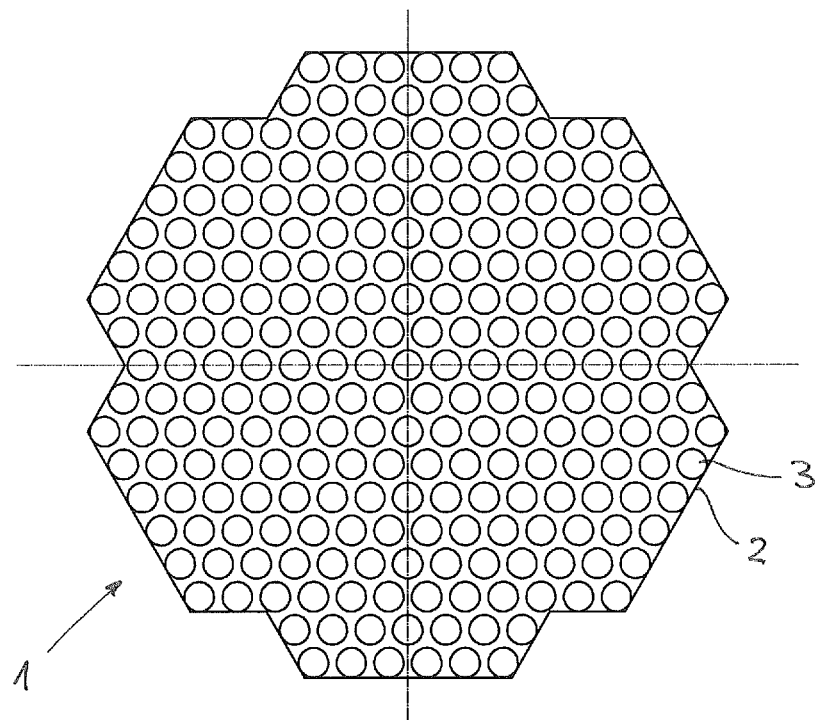
FIG. 3 is a schematic cross-sectional view of a tube apparatus according to a second embodiment of the invention.
Figure 4:
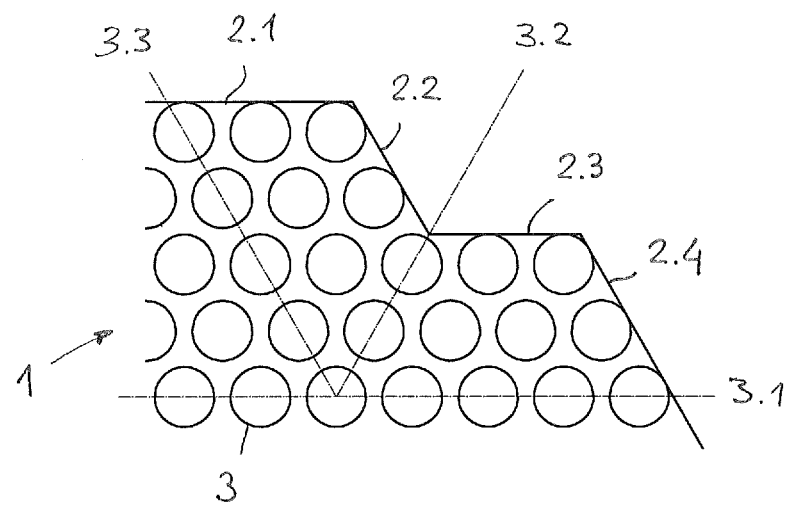
FIG. 4 shows a detail of FIG. 3.

FIGS. 3 and 4 show a variation of embodiment with tubes having a triangular pitch. For the sake of simplicity the same reference numbers as those in FIG. 1 are used.

The shell 2 has a cross-section of an irregular polygon with 18 sides. The directional lines of the tubes 3.1, 3.2 and 3.3 in the cross-sectional plane are spaced at angles of 60°, i.e. for example are oriented at angles of 0, 60 and 120 degrees with respect to a reference direction parallel to the direction 3.1. In the detail shown in FIG. 3 it can be seen that the side 2.1 is parallel to the directional line 3.1, the side 2.2 is parallel to the directional line 3.3 and so on.

Figure 5:
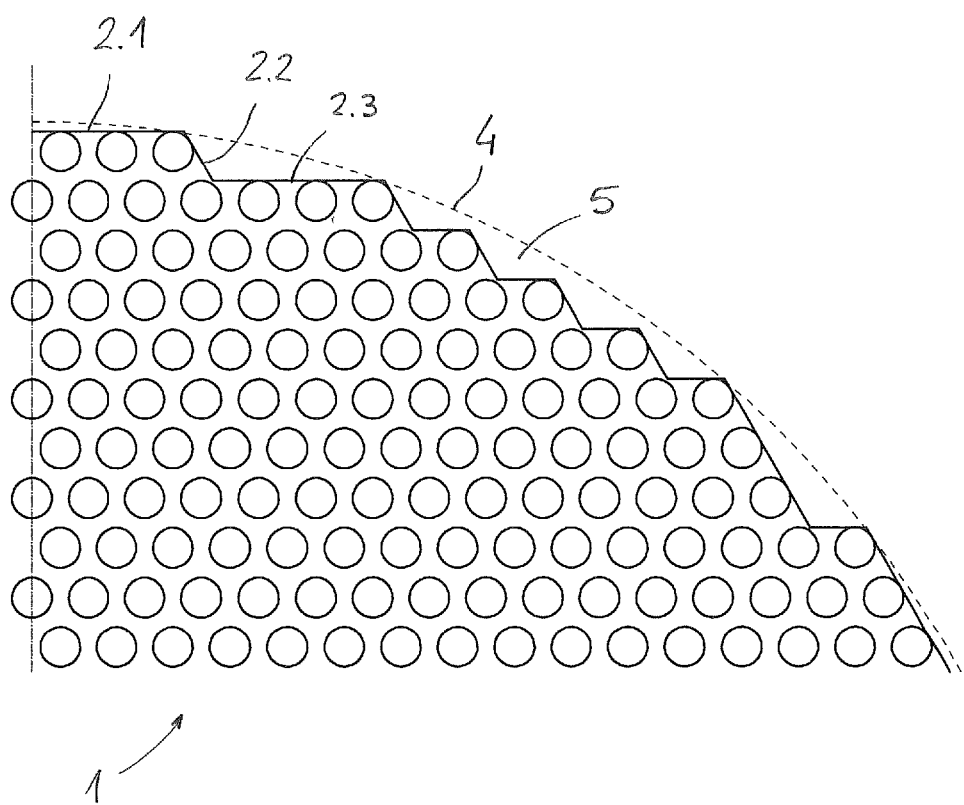
FIG. 5 shows a schematic cross-sectional view according to a third embodiment.

FIG. 5 shows a detail of a shell 2 with a greater number of sides, in particular 60 sides with a triangular tube pitch. It can be seen that the stepped shell 2 closely matches a cylindrical shell, the cross-section of which is indicated by the broken line 4 in the figure. The stepped shell, however, has the advantage that it does not leave bypass areas such as for example the zone indicated by 5.

Figure 6:
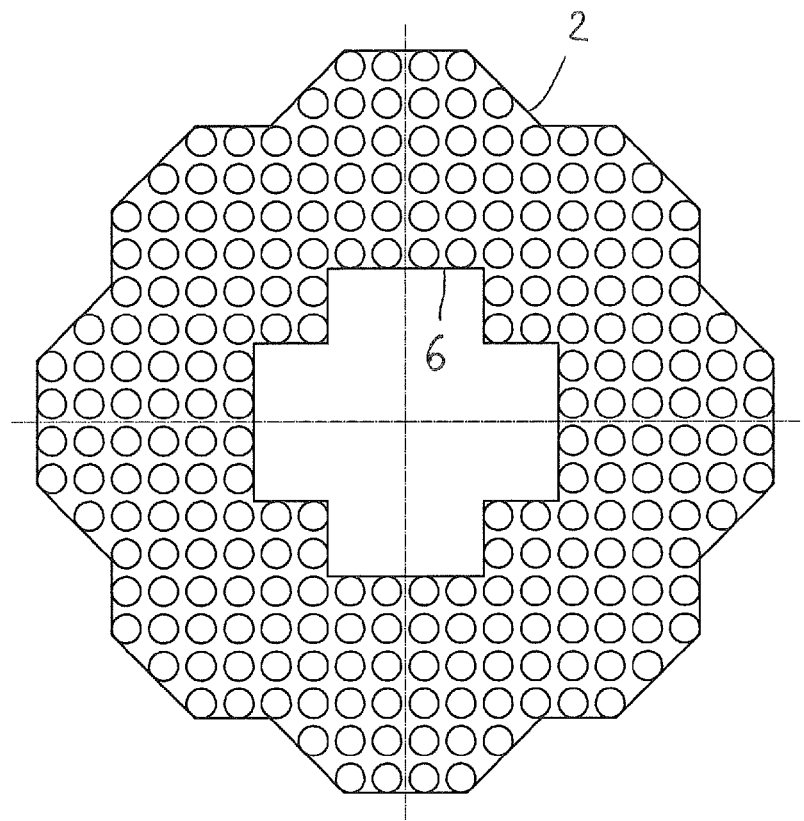
FIG. 6 shows a schematic cross-sectional view of a tube apparatus according to a further embodiment, with a central duct.

FIG. 6 shows an embodiment in which the apparatus also comprises a central duct 6. The tube bundle 1 therefore is arranged in a ring between the shell 2 and the duct 6. Advantageously, the duct 6 also has a stepped cross-section with sides parallel to the directional lines of the tubes, in accordance with that described above.

The sides of the cross-sectional polygon of the internal duct are also multiples of the parameter which expresses the pitch of the tubes and are parallel to the directional lines of the tubes. The number of sides (i.e. faces) of the internal duct is not necessarily equal to the number of sides of the outer shell; preferably it is smaller.

Figure 7:
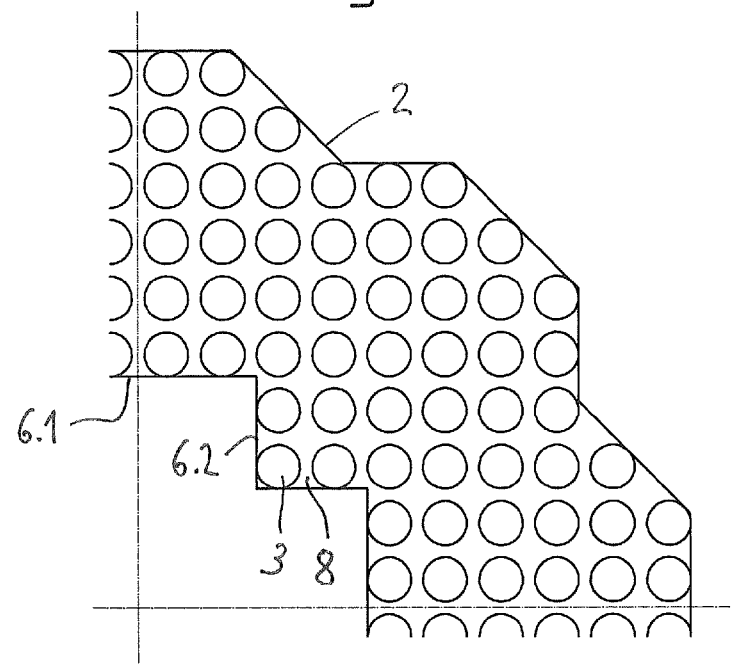
FIG. 7 shows a detail of FIG. 6.

For example in FIG. 7 two sides 6.1, 6.2 of the duct 6 are shown. The duct 6 has a cross-section with 12 sides, while the shell 2 has a cross-section with 24 sides.

The design of the internal duct 6 also with a stepped cross-section has the further advantage of allowing a certain number of additional tubes to be accommodated. This advantage is shown in FIG. 7: it may be noted that, owing to the stepped form of the duct 6, a useful volume 8 for housing three tubes may be recovered.

The illustration in FIG. 6 is provided purely by way of example and the advantage of displacing the tubes from the periphery to the centre may be more evident in the case of apparatus provided with a larger number of tubes.

Figure 8:
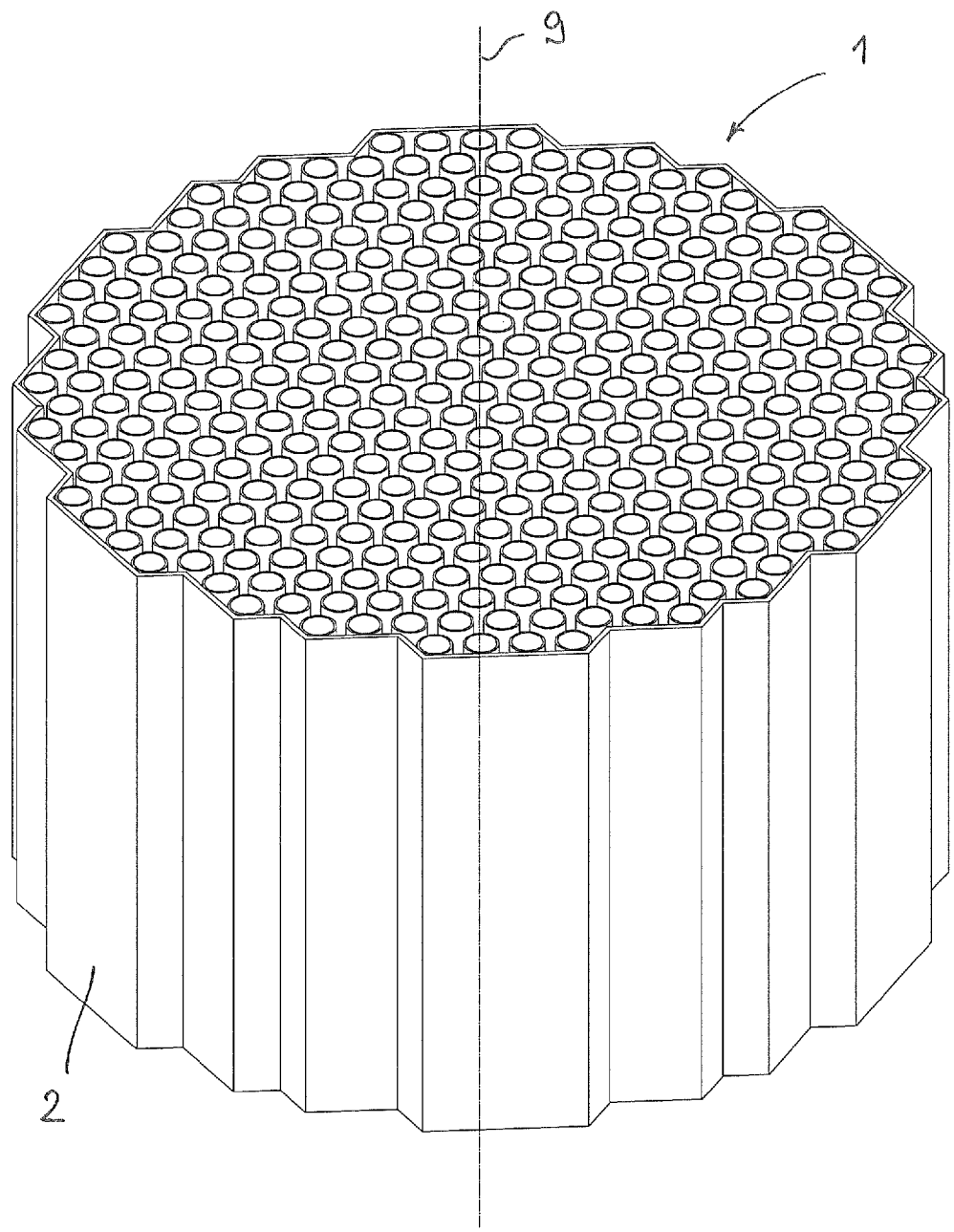
FIG. 8 is an axonometric view of a portion of a tube bundle according to one of the various embodiments of the invention.

FIG. 8 shows a simplified axonometric view of a tube bundle with a triangular pitch, provided with a shell 2 according to the invention. The figure also shows the axis 9 of the tube bundle (which is parallel to the tubes 3); the cross-sections shown in FIGS. 1-7 are cross-sections along planes perpendicular to said axis 9.

The invention claimed is:

1. A heat exchanger comprising a tube bundle and a shell which surrounds said tube bundle, said tube bundle comprising tubes arranged with a square or triangular pitch, wherein:
   said shell has a cross-section, in a plane perpendicular to said tubes, having the form of an irregular polygon;
   said cross-sectional polygon has a number of sides which is a multiple of three when the tubes have a triangular pitch and is a multiple of four when said tubes have a square pitch,
   the sides of said cross-sectional polygon of the shell are parallel to directional lines of the tubes of said bundle;
   wherein the heat exchanger comprises a central duct, wherein the tubes of the bundle are arranged in a ring between said shell and said central duct.

2. The heat exchanger according to claim 1, wherein the tubes of the bundle have a square pitch, and said directional lines of the tubes are straight lines in a plane perpendicular to the axis of the tubes, having directions spaced at angles of 45 degrees.

3. The heat exchanger according to claim 1, wherein the tubes of the bundle have a triangular pitch, and said directional lines of the tubes are straight lines in a plane perpendicular to the axis of the tubes, having directions spaced at angles of 60 degrees.

4. The heat exchanger according to claim 1, wherein said central duct also has a cross-section, in a plane perpendicular to said tubes, having the form of an irregular polygon, and wherein:
   said cross-sectional polygon of said duct has a number of sides which is a multiple of three when said tubes have a triangular pitch and is a multiple of four when said tubes have a square pitch, and
   the sides of said cross-sectional polygon of the duct are also parallel to directional lines of the tubes of said bundle.

5. The exchanger according to claim 4, wherein the number of the sides of the cross-sectional polygon of the duct is smaller than the number of sides of the cross-sectional polygon of the shell.

6. The exchanger according to claim 1, wherein the tube bundle is extractable from the shell.

7. The exchanger according to claim 1, wherein the tube bundle comprises baffles for supporting the tubes and for preventing vibrations.

8. The heat exchanger according to any claim 1, for use as an internal exchanger of pressurized apparatus or chemical reactors.

9. A pressurized apparatus, such as a chemical reactor and preferably a catalytic reactor for the synthesis of ammonia or methanol, comprising a heat exchanger according to claim 1.

\* \* \* \* \*